(12) United States Patent
Kay et al.

(10) Patent No.: US 7,896,857 B2
(45) Date of Patent: Mar. 1, 2011

(54) URINE COLLECTION ASSEMBLY

(75) Inventors: Dennis M. Kay, Tampa, FL (US); Brian P. Fee, Palm Harbor, FL (US)

(73) Assignee: BioDerm, Inc., Largo, FL (US)

( * ) Notice: Subject to any disclaimer, the term of this patent is extended or adjusted under 35 U.S.C. 154(b) by 10 days.

(21) Appl. No.: 10/961,396

(22) Filed: Oct. 12, 2004

(65) Prior Publication Data

US 2006/0079854 A1    Apr. 13, 2006

(51) Int. Cl.
*A61M 1/00* (2006.01)
*A47K 11/00* (2006.01)

(52) U.S. Cl. .......................... 604/317; 4/144.1; 4/144.3
(58) Field of Classification Search .......... 604/317–331; 4/144.1, 144.3
See application file for complete search history.

(56) References Cited

U.S. PATENT DOCUMENTS

| | | | |
|---|---|---|---|
| 3,312,221 A * | 4/1967 | Overment | 604/317 |
| 4,449,971 A * | 5/1984 | Cawood | 604/544 |
| 5,263,946 A * | 11/1993 | Klug | 604/327 |
| 5,263,947 A | 11/1993 | Kay | |
| 5,267,989 A | 12/1993 | Moyet-Ortiz | |
| 5,380,312 A | 1/1995 | Goulter | |
| 5,409,474 A | 4/1995 | Fleeman-Hardwick | |
| 5,618,277 A | 4/1997 | Goulter | |
| 5,713,880 A | 2/1998 | Anderson | |
| 5,797,890 A | 8/1998 | Goulter et al. | |
| 5,827,247 A | 10/1998 | Kay | |
| 5,830,932 A | 11/1998 | Kay | |
| 6,045,542 A * | 4/2000 | Cawood | 604/327 |
| 6,113,582 A | 9/2000 | Dwork | |
| 6,179,818 B1 * | 1/2001 | Kydonieus et al. | 604/332 |
| 6,223,751 B1 | 5/2001 | Park | |
| 6,296,627 B1 * | 10/2001 | Edwards | 604/347 |
| 6,679,867 B2 * | 1/2004 | Miskie | 604/349 |
| 6,793,651 B1 * | 9/2004 | Bennett et al. | 604/544 |
| 2003/0149408 A1 * | 8/2003 | Levinson | 604/329 |
| 2004/0034335 A1 * | 2/2004 | Dolan | 604/544 |

OTHER PUBLICATIONS

"The Belly Bag®", Rüsch, www.originalbellybag.com, printed Jul. 7, 2004, 9 pp.
"Incontinent Men are Dry and Free Again!", AlphaDry, www.alphadry.com (2004-2005), 2 pp.
"The Belly Bag®" advertisement, Rüsch, printed prior to Oct. 12, 2004, 1 pp.

* cited by examiner

*Primary Examiner* — Melanie J Hand (57) ABSTRACT

A urine collection assembly includes a urine collection device and a urine collection chamber in communication with the urine collection device. The urine collection chamber includes a collection reservoir, an entrance conduit having an inlet to receive urine from the urine collection device and an outlet terminating in the reservoir, an anti-reflux valve, and an exit conduit. The collection reservoir is configured to be wearable in close proximity to a user's body below the waist and above the knees of the user. The collection reservoir holds urine excreted from a user. The exit conduit enables drainage of the collection reservoir. The exit conduit also enables attachment of the collection reservoir to an additional conventional urine collection chamber. The anti-reflux valve is configured to prevent urine from backing up out of the urine collection chamber and into the urine collection device. The inlet of the urine collection chamber is disposed in close approximation to the urine collection device to direct urine from the urine collection device to the collection reservoir. The urine collection assembly further can include a support device wearable by the user to bear the weight of the urine collection chamber and to support the inlet of the urine collection chamber in close approximation to the urine collection device.

9 Claims, 7 Drawing Sheets

URINE COLLECTION ASSEMBLY

BACKGROUND OF THE INVENTION

The present invention relates to a urine collection assembly. More specifically, the present invention relates to a urine collection chamber adapted to be worn in the area of a user below the waist and above the knees.

A urine collection device is defined in this document as a device that is attached to or inserted into a user's body for the purpose of urine collection, including but not limited to urinary catheters, Foley catheters, Suprapubic catheters, nephrosotomy catheters, condom catheters and external incontinence devices. These urine collection devices can be indwelling, such as Foley catheters, or attached externally to the user, such as the condom catheter and the external incontinence devices disclosed in U.S. Pat. No. 5,263,947, U.S. Pat. No. 5,827,247, and U.S. Pat. No. 5,830,932, each of which is hereby incorporated by reference in its entirety. Urine excreted from the user's body and collected by the urine collection device is accumulated in a urine collection chamber, such as a urine collection leg bag. Current commercial urine collection chambers are located some distance from the urine collection devices, and urine is directed from the urine collection devices to the remote collection chambers via intermediary urine drainage tubing or hoses. In this regard, the urine collection chamber typically is connected to the urine collection device by intermediary tubing ranging from approximately 18 to 42 inches in length.

There are several problems associated with a urine collection chamber being distant from the urine collection device. One such problem, defined herein as the Urine Backup Phenomenon, occurs when urine backs up or fails to drain from the urinary drainage tubing.

As a consequence of the "back up" of urine in the urinary drainage tubing, urine reflux can occur; that is, urine can return through the urinary drainage tubing, to the catheter, and into contact with the user. Users with indwelling catheters can incur bladder infections as bacterial growth may occur in the already excreted urine that is refluxed back into the bladder via the indwelling catheter. Users with external catheters can incur urinary-tract infections, skin maceration, and premature dislodgment of the catheter.

An additional problem related to backflow of urine is generated when the urine collection chamber is positioned adjacent the abdominal area, such as described in U.S. Pat. No. 4,449,971. In this regard, a user wearing an external urine collection device may experience backflow of urine from the abdominal urine collection chamber and from the chamber's proximal urinary drainage tubing into the external device due to the effects of gravity and periodic variations of intra-abdominal and bladder pressure. This backflow can cause dislodgment of an external device and increase duration, amount and pressure of skin exposure to urine, resulting in moisture-related skin complications, such as maceration of the skin and premature dislodgement of the external device. Furthermore, a user employing an indwelling urine collection device may experience increased retention of urine in the bladder and/or increased stasis of urine in the indwelling device. This may lead to occurrences of urinary tract infections.

Another problem associated with the urine collection chamber being distant from the urine collection device relates to social privacy. An individual using such a collection chamber has limited clothing options and may perceive the collection chamber as indiscreet and visible to others. Many individuals avoid the use of such remote collection chambers and are forced to use incontinence pads or briefs that contribute to skin breakdown, wounds, urinary tract infections, leakage, odor and the resulting social isolation.

Thus, there is a need for an improved urine collection chamber for use in a urine collection assembly that addresses the problems associated with known urine collection assemblies.

A fluid collection device is defined in this document as a device that is attached to or inserted into a user's body for the purpose of fluid collection, including but not limited to pleurocentesis catheters, biliary tree drainage stents, wound drains and stents. Fluid drained from a user and collected by a fluid collection device typically is accumulated in a fluid collection chamber.

A problem associated with known fluid collection chambers relates to maintaining their specific intended connection to a user's body. For example, a Jackson-Pratt drain consists of plastic tubing with multiple perforations that is left inside the wound. The drain is introduced through a separate stab wound and sutured to the skin. It then is connected to a collection chamber that is squeezed and emptied of its contents. The collection chamber may be secured by a safety pin attached to a surgical gown. Movement of the gown may cause dislodgement of the drain or injury to the drainage attachment site.

Thus, there is a need for an improved fluid collection chamber for use in a fluid collection assembly that addresses the problems associated with known fluid collection assemblies.

SUMMARY OF THE INVENTION

An aspect of the present invention relates to a urine collection assembly. The urine collection assembly includes a urine collection device and a urine collection chamber communicating with the urine collection device. The urine collection device may be an indwelling or Foley catheter, a condom catheter or an external incontinence device, such as described by U.S. Pat. No. 5,263,947, U.S. Pat. No. 5,713,880, U.S. Pat. No. 5,827,247, and U.S. Pat. No. 5,830,932. The urine collection chamber comprises a collection reservoir configured to be wearable in close proximity to the body below the waist and above the knees of a user and to hold urine excreted from a user. The collection chamber can have an entrance conduit, and the entrance conduit can have an inlet to receive urine from the urine collection device. The entrance conduit also can have an outlet terminating in the collection reservoir. The urine collection chamber further can comprise an anti-reflux valve communicating with the entrance conduit to receive urine from the entrance conduit. The anti-reflux valve can prevent reflux of urine or negative pressure into the lumen of the urine collection device and can direct urine into the collection reservoir of the urine collection chamber. The urine collection chamber also can comprise an exit conduit. The exit conduit can include a plug or cap closure to open or close the lumen of the exit conduit. When the exit conduit is closed, urine can collect in the collection reservoir. When the exit conduit is open, urine can be drained from the collection reservoir. The exit conduit can be composed of resilient material with the appropriate dimension for optional releasable attachment to a connector of drainage tubing of an additional urine collection chamber, such as a urine collection leg bag, providing for additional urine collection capacity by the addition of the urinary drainage tubing and the additional urine collection chamber.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and, together with the description, serve to explain the principles of the invention.

DETAILED DESCRIPTION OF THE PREFERRED EMBODIMENTS

Reference will now be made in detail to embodiments of the invention, examples of which are illustrated in the accompanying drawings. An effort has been made to use the same reference numbers throughout the drawings to refer to the same or like parts.

Figure 1:
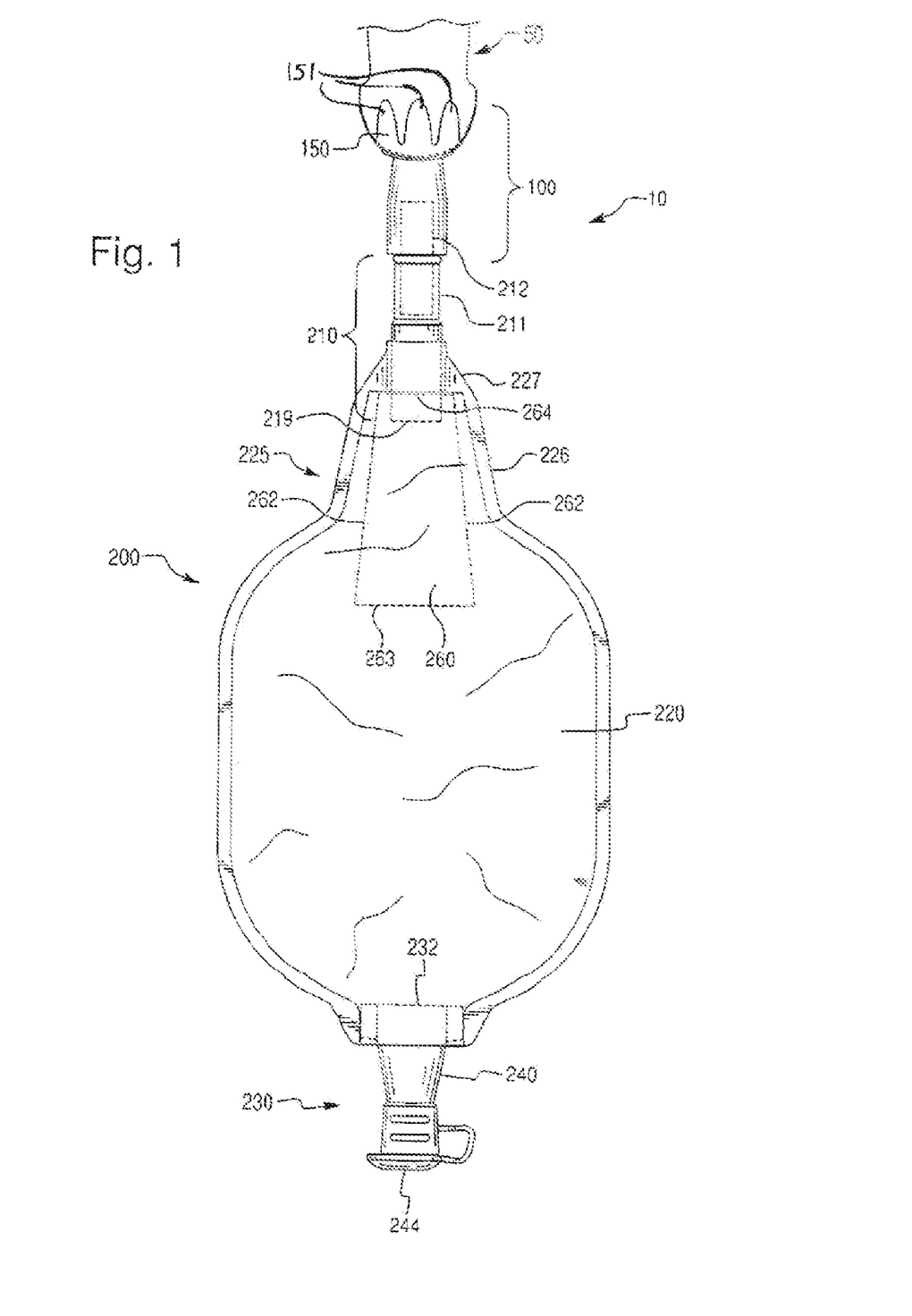
FIG. 1 is a front elevation view of a urine collection chamber connected to a urine collection device according to an embodiment of the invention.

FIG. 1 illustrates a urine collection assembly 10. The urine collection assembly 10 generally includes a urine collection device, such as the external incontinence device 100 shown in FIG. 1, and a urine collection chamber 200 in accordance with the invention. This assembly 10 addresses problems with known urine collection assemblies, including the undesirable phenomena referred to in this application as the Siphon Effect and the Urine Backup Phenomenon.

A significant problem caused by known urine collection assemblies is a previously unrecognized phenomenon described herein as the Siphon Effect. The Siphon Effect, so described herein, refers to a barometric phenomenon whereby negative pressure accumulates in the urinary drainage tubing and urine collection chamber of a conventional urine collection assembly. The Siphon Effect phenomenon occurs as urine descends through the relatively long lengths of urinary drainage tubing, present in known urine collection assemblies, that directs urine from the urine collection device to the urine collection chamber. As expelled urine descends through the urinary drainage tubing and drops into the urine collection chamber, normally located approximately 18 to 42 inches below the user's urinary meatus, negative intra-luminal pressure accumulates behind the column of urine, causing partial vacuum forces within the lumen of the tubing. In the case of external catheter users, the vacuum forces draw external genito-urinary tissue toward the proximal end of the urinary drainage tubing, at times causing skin irritation, swelling, ecchymosis and suction force injuries of the genito-urinary tissue. Shorter duration of effective device function (reduced wear time) or premature detachment of external catheters may also result from the suction caused by the Siphon Effect. In the case of indwelling catheter users, it is hypothesized that the vacuum forces generated by the Siphon Effect impinge on the inner (mucosal) surface of the bladder by drawing bladder vesicle neck tissue into the drainage port (eyes) of the indwelling catheter, resulting in vesicle neck irritation, a known phenomenon associated with indwelling catheter use. Vesicle neck irritation has been hypothesized to enhance bacterial colonization of the bladder, enhancing the risk of urinary catheter associated urinary tract infections. The urine collection assembly 10 is constructed to address such problems with known urine collection assemblies.

The Urine Backup Phenomenon is a result of the increased relative negative pressure in the collection chamber relative to the barometric pressure within the lumen of the drainage tube. As aliquots of urine descend through the tubing, negative pressure is generated within the lumen of the tube and within the lumen of the collection bag. Many urine collection chambers are constructed with an anti-reflux valve through which the urine must pass to enter the collection chamber. As these aliquots of urine drop through the anti-reflux valve and into the collection chamber, the anti-reflux valve prevents equalization of the relative negative pressure between the drainage tubing and the collection chamber. Since the collection chamber may hold fifty times the volume of the tubing, many aliquots of urine, and increasing amounts of relative negative pressure, are delivered to the collection chamber. The relative negative pressure in the collection chamber may become much greater than the negative pressure in the drainage tubing. This greater relative negative pressure in the collection chamber can cause the anti-reflux valve located in the collection chamber to remain closed, requiring greater force for the urine to exit the tubing when passing through the anti-reflux valve. Due to this relative increase in negative pressure within the collection chamber, urine "backs up" in the urinary drainage tubing above the anti-reflux valve of the collection chamber. This backup of urine may cause urine reflux into the urine collection device, and possibly may push urine into contact with the user, creating the above-stated problems associated with urine reflux.

Figure 2:
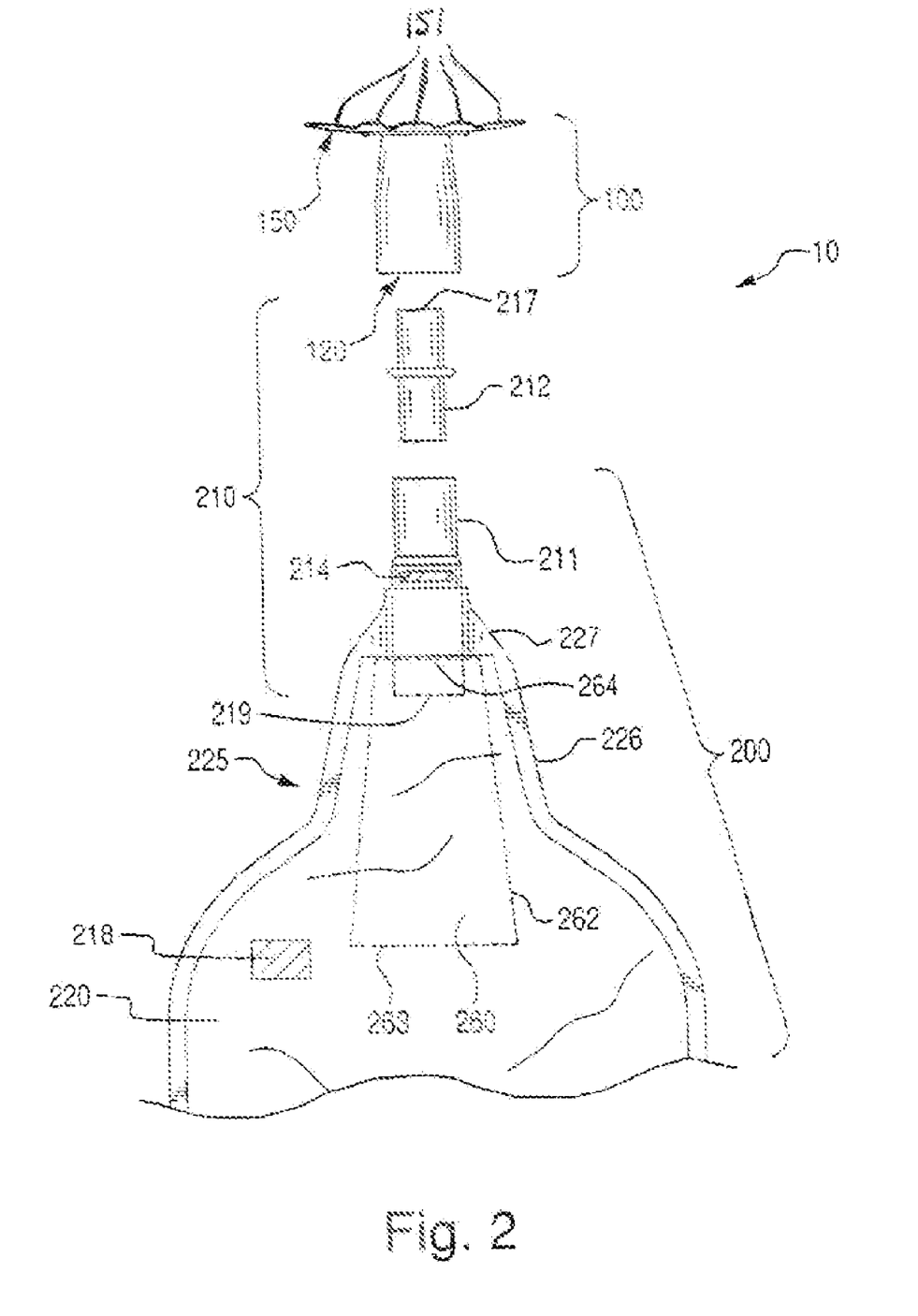
FIG. 2 is an exploded, detail view of a urine collection device, the entrance conduit of the urine collection chamber of FIG. 1, and a portion of the collection reservoir of the urine collection chamber of FIG. 1.

FIG. 1 illustrates a urine collection chamber 200 in accordance with the invention that communicates with a urine collection device 100 mounted to a user's penis 50. Although FIG. 1 illustrates the urine collection chamber 200 in association with male anatomy, it will be understood that the urine collection chamber 200 also can be used by females. The urine collection chamber 200 generally includes a collection reservoir 220, an entrance conduit 210, an anti-reflux valve 260, and an exit conduit 230, as will be described in detail below. The urine collection chamber 200, and, more particularly, the inlet 217 of the urine collection chamber 200 (as shown in FIG. 2), is configured to be disposed in close approximation to the urine collection device 100; that is, the urine collection chamber 200 is configured either to connect directly to the urine collection device 100 or to be indirectly connected and spaced from the urine collection device 100 by intermediary tubing that is sufficiently short so as to prevent the Siphon Effect.

The urine collection assembly 10 thus does not require any intermediary structure between the urine collection device 100 and the urine collection chamber 200. In particular, an embodiment of the present invention contemplates the absence of the tubing that, in conventional urine collection assemblies, is required to connect a urine collection chamber to a urine collection device. For example, the assembly of U.S. Pat. No. 4,449,971 will not function effectively while in close approximation (for example, connected directly without additional intermediary tubing) to an external urine collection device when the collection device is attached to the user at the appropriate anatomical application site for effective use of that assembly.

Elimination of the requirement for intermediary tubing provides specific unforeseen advantages. Excreted urine can build up hydrostatic pressure in the intermediary tubing, particularly in positions where the intermediary tubing and the entry point into the collection chamber are above the point at which urine leaves the user's body. In the case of the assembly disclosed in U.S. Pat. No. 4,449,971, these positions include sitting, standing and lying supine. Urine dwelling in the lumen of the intermediary tubing can back up into the collection device due to gravity and hydrostatic pressure. This presence of additional excreted urine (under gravitational pull and hydrostatic pressure) exerts force against the seal between the external urine collection device and the user's skin, causing premature detachment (reduced wear time) as well as increased opportunity for infection, skin irritation or breakdown and sudden dislodgement of the external urine collection device. By comparison, the subject invention provides a urine collection chamber that enables collection of urine from a urine collection device, without requiring generation of hydrostatic pressure to drive the urine upward into the urine collection chamber.

The collection reservoir 220 of the urine collection chamber 200 is configured to be wearable in close proximity to the user's body, below the waist and above the knees of the user, and thus can be concealed discretely under clothing. The collection reservoir 220 is configured to be wearable in the pre-pubic to the perineal area of a user, between the user's thighs, where the thighs meet the pelvis. The pre-pubic to perineal area extends from the portion of the body at the base of the male penis or the female mons pubis to the anus. More specifically, the pre-pubic to perineal area is bordered by the most superior aspect of the symphosis pubis, the distal aspect of the coccyx, and bordered laterally by the proximal medial thighs. The collection reservoir 220 can be of a size to occupy the entire pre-pubic to perineal area or, alternatively, it can be sized to occupy just a portion of that area.

The collection reservoir 200 is of a shape and a composition to conform to the ergonomic requirements for placement in the pre-pubic to the perineal area. The shape of the collection reservoir 220 is generally elliptical, although other shapes are envisioned, and can include a tapered neck portion 225. The elliptical shape of the collection reservoir 220 conforms to the complex curves of the pre-pubic to perineal area, which vary from user to user.

Figure 4:
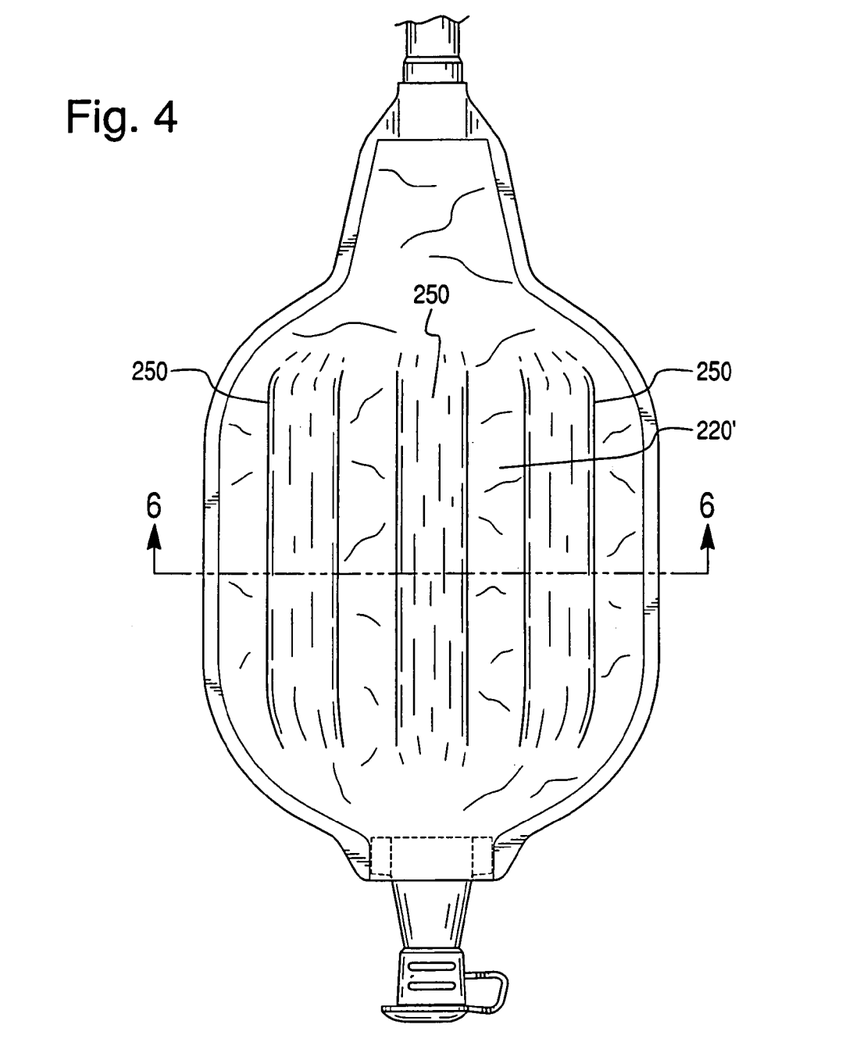
FIG. 4 is a front elevation view of an embodiment of the urine collection chamber with pleats for increased capacity.
Figure 5:
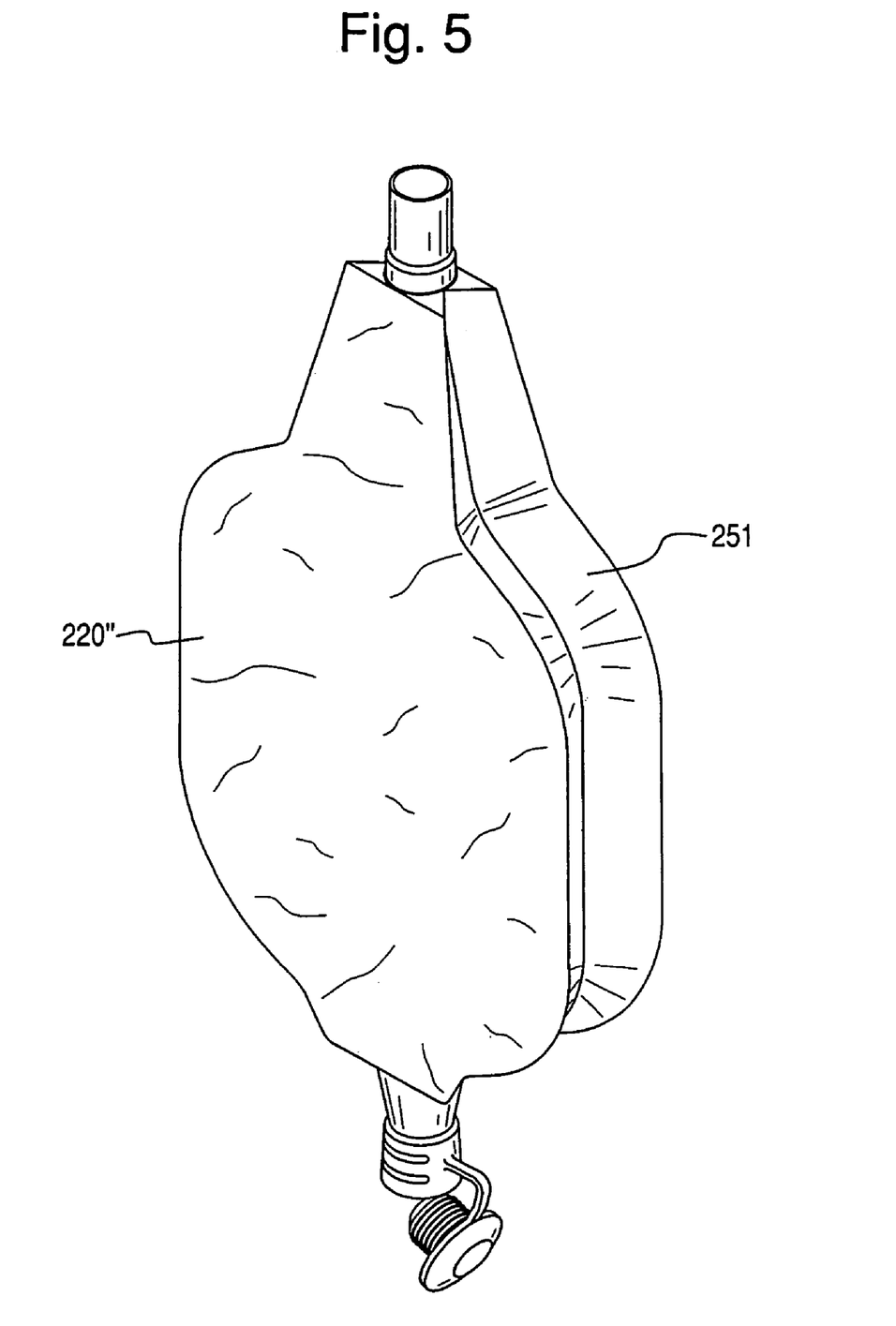
FIG. 5 is a perspective view of an embodiment of the urine collection chamber with gussets for increased capacity.
Figure 6:
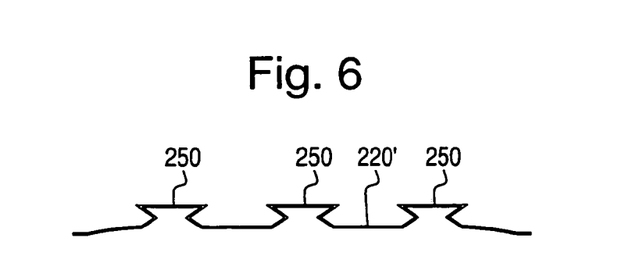
FIG. 6 is a cross-sectional view of the pleats of the urine collection chamber of FIG. 4, taken along line 6-6 of FIG. 4.

The collection reservoir 220 can have a volume consistent with the management of mild to moderate incontinence, i.e., less than 500 cc output per urine loss event. For example, the collection reservoir 220 can hold 250 cc of fluid. Further, as shown in FIGS. 4-6, the collection reservoir 220 can include gussets 251 or pleats 250 or folds to provide greater collection capacity, while maintaining a compact profile, capable of fitting in a user's pre-pubic to perineal area. FIGS. 4 and 6 illustrate a collection reservoir 220' that includes a plurality of pleats 250. The pleats 250 can be located on both the front side and the back side of the collection reservoir 220' (FIG. 4 does not show the anti-reflux valve 260 for ease of illustration of pleats 250). FIG. 5 illustrates a collection reservoir 220" that includes side gussets 251.

As can be seen in FIG. 1, the collection reservoir 220 can be formed by two sheets of film sealed at the edges. Suitable films may include, for example, polyvinyl chloride (PVC) or a high ethylene vinyl acetate (EVA) multi-laminate film, such as polyvinylidene chloride (PVDC). The collection reservoir 220 can be between 2-10 mil in thickness. For example, the collection reservoir is 4-10 mil thick when composed of a PVC film, or 2-5 mil thick when composed of PVDC film. In one embodiment, the collection reservoir 220 is 6 mil thick and composed of a PVC film. The film of the collection reservoir 220 is a fluid-impervious material to create a fluid-tight urine containment area. In addition, the film of the collection reservoir 220 can include a non-woven material panel on an outer surface of the reservoir proximate to the wearer's skin to increase user comfort and prevent accumulation of perspiration between the user's skin and the film of the collection reservoir. Further, the collection reservoir 220 can be composed of material with odor barrier capabilities.

The tapered neck portion 225 of the collection reservoir 220 narrows as it approaches the entrance conduit 210. In one embodiment, as illustrated in FIGS. 1 and 2, the tapered neck portion 225 can include a first tapered portion 226 and a second, more acutely tapered portion 227. The tapering of portions 226 and 227 minimizes the potential for skin injury to the user and maximizes comfort for the user, as will be described in more detail below.

To direct urine into the collection reservoir 220, the urine collection chamber 200 includes an entrance conduit 210. The entrance conduit 210 can be composed of tubing extruded from a material resin similar to that of the collection reservoir 220, for example, PVC. The entrance conduit 210 can be contiguous with the neck portion 225 of the collection reservoir 220, as seen in FIG. 2. The entrance conduit 210 provides a flexible, narrow and low profile entry into the collection reservoir 220. The entrance conduit 210 can include an entrance port 211 and an adaptor 212 separably connectable to the entrance port 211 and to an outlet 120 of the urine collection device 100. Alternatively, the entrance conduit 210 can be formed by a single conduit structure, or the adaptor 212 can be permanently attached to the entrance port 211. The entrance conduit 210 has an inlet to receive urine from the urine collection device 100, such as inlet 217 of adaptor 212, and an outlet terminating in the collection reservoir, such as outlet 219 of entrance port 211. As mentioned above, the inlet is disposed in close approximation to the urine collection device 100, being either directly connected to the urine collection device 100 or coupled to the urine collection device 100 by tubing sufficiently short to prevent the Siphon Effect.

The entrance conduit 210 is configured so that the urine collection chamber 200 can be employed with either an indwelling urine collection device, such as a Foley catheter, or with an external device, such as the external incontinence device shown in FIG. 1 and described in U.S. Pat. No. 5,263,947. In this regard, the entrance conduit 210 can receive the distal end of an indwelling catheter, or it can connect in an interference fit with the outlet of an external incontinence device. In the embodiment shown in FIGS. 1 and 2, the adapter 212 of the entrance conduit 210 is configured to connect to external incontinence device 100, which includes a faceplate 150 having a plurality of 151 for external attachment to a parameatal surface of a user's penis and an outlet conduit 120 for urine drainage. The parameatal surface is that surface which comprises the urethral meatus and surrounding skin or mucosal tissue near the urethral meatus, the urethral meatus being the external opening of the urethra. The external incontinence device 100 creates a parameatal seal with the parameatal surface. The external urine collection device thusly collects urine at the site, i.e. the urethral meatus, where urine is released external to the user's body. The adaptor 212 establishes an interference fit and seal with the outlet conduit 120 of the external incontinence device 100 and also establishes an interference fit and seal with the entrance port 211. The adaptor 212 can be configured to provide an interference fit with the distal end of either an indwelling catheter or a condom catheter. In one embodiment, the adaptor 212 can be a stepped adaptor.

The entrance conduit 210 and the tapered neck portion 225 of the collection reservoir 220 are configured to accommodate male retracted anatomy. Male retracted anatomy can occur when the penis retracts into the abdominal fat pad (i.e., the panniculus adiposis) or the scrotum due to, for example, obesity, age, or short penile shaft length. Penile retraction can occur in the sitting position or when a seated man leans forwards. Male retracted anatomy describes the condition in which none or only a small portion of the penis extends beyond the panniculus adiposis or scrotum in certain body positions, such as sitting, lying or standing. In this regard, the cross sections of entrance conduit 210 and of tapered neck portion 225 are narrow, and the entrance conduit 210 and the neck portion 225 are flexible and able to ergonomically conform to the retraction channel of male retracted anatomy. The retraction channel is herein defined as the tract of skin or space formed around the penis by the panniculus or scrotum as the penis retracts. Further, the slim profile of the entrance conduit 210 requires minimal contact with skin; the smooth, streamlined and tapered neck portion 225 minimizes the potential for skin injury; and the cross-sectional areas of the entrance conduit 210 and the neck portion 225 are minimal to enable the urine collection assembly 10 to stay with the penis as it retracts into the retraction channel. In one embodiment, the urine collection assembly 10 has a minimal cross-sectional area such that any point within three inches of the attachment site 150 of the urine collection device 100 to the penis 50 has no cross-sectional dimension exceeding two inches, and the entrance conduit 210 has no cross-sectional dimension exceeding three inches, and more preferably no cross-sectional dimension exceeding ¾ inch. In addition, the entrance conduit 210 and the neck portion 225 comprise an externally smooth contour; that is, these structures have no ridges or raised areas that could damage or irritate skin proximate to intended locations of use of the urine collection assembly 200 or of urine collection chamber 220.

The entrance conduit 210 and the tapered neck portion 225 of the collection reservoir 220 also can be configured to accommodate female retracted anatomy. Female retracted anatomy can occur when the female urinary meatus is located intravaginally or within the vaginal verge. Further, involution of the female urinary meatus can occur with changes in body position and/or due to body habitus. For example, an obese woman may have shifts in the position of her urinary meatus due to pressure from an enlarged panniculus adiposus, mons pubis, or labia majora, particularly during shifts in body position, for example, from lying to sitting or from sitting to standing. In this regard, the cross sections of entrance conduit 210 and tapered neck portion 225 are narrow, and the entrance conduit 210 and the neck portion 225 are flexible and able to ergonomically conform to the retracted position of the urinary meatus.

The entrance conduit 210 and the tapered neck portion 225, in particular the second tapered portion 227, may include radiused welds (not shown) to minimize irritation, injury or laceration of the skin or tissue lining or contiguous with the retraction channel.

The entrance conduit 210 and the tapered neck portion 225 of the urine collection assembly 10 also are configured to benefit a person who is moving throughout the course of the day. In this regard, the relevant body surfaces of the user go through a wide range of anatomical shape changes during a day—standing, sitting, lying, penile erections, etc. Seating position changes may alter a user's anatomy in size, volume, dimension and pressure. Dimensions of the pre-pubic to perineal area vary within and among users as each user's anatomy has complex curves and the shape of a user's lower abdominal area, thighs and perineal area may change while seated or while moving to other body positions. Pressure also may be exerted on a user's penis and surrounding area. Further, the seated individual has a reduced open space adjacent to the pre-pubic to perineal area to accommodate a urine collection device and/or urine collection chamber. The narrow shape and minimized cross-sectional area of the entrance conduit 210 and neck portion 225 of urine collection reservoir 220 are configured to adapt to the changes in shape and position of a user. Furthermore, the entrance conduit 210 has a durometer, or hardness measurement, and flexural modulus, or flexibility, compatible with the ergonomic requirements for placement in the pre-pubic to perineal area, particularly the flexibility required during sitting and body position changes. In one embodiment, the entrance conduit 210 is comprised of material with a durometer measurement of less than or equal to 60 Shore A durometer. In one embodiment, if any component of the entrance conduit 210 is comprised of a material with a Shore A durometer greater than 60, that component is no larger than 1.25 inches in length.

The entrance conduit 210 combined with the flexibility of neck portion 225 and collection reservoir 220 also reduces and, in some cases, eliminates, a previously undescribed "torque effect" that can occur during the use of known urinary drainage connectors employed for delivery of urine into the drainage tubing of known urinary collection bags. In this regard, the drainage tubing of known urine collection chambers has relatively inflexible entrance ports that can transmit torque or potentially dislodging flexion forces to the urine collection device. When such a known urine collection chamber's drainage connector is connected to an external catheter, such as a condom catheter, this torque effect can cause blocked urine outflow due to kinking or twisting of the outlet portion of the condom catheter, which can result in ballooning of the condom catheter filled with trapped urine or blow-off (detachments) of the catheter from the user. An additional consequence of torque placed on the external catheter is that the external catheter may become dislodged within a shorter duration of effective use (wear time) than would be possible with reduced or absent torque. When such a known urine collection chamber's drainage connector is connected to an indwelling catheter, torque forces transmitted to the indwelling catheter, and thereby against the meatus, may result in tearing and stretching of the meatus and injury to the urinary tract. Acquired hypospadius, a torn or enlarged urinary meatus, is a well known complication of indwelling urethral catheters. By comparison, the flexible entrance conduit 210 and contiguous components of the urine collection chamber 200 can flex more easily than urinary drainage connectors of known urine collection chambers. Therefore, the entrance conduit 210 significantly reduces the torque forces that have the potential to interfere with the interface of a urine collection device and the user's anatomy. For the purposes of this application, minimized torque and dislodging forces are defined as torque and dislodging forces less than those that would be exerted by a belly bag, such as described in U.S. Pat. No. 4,449,971, or a leg bag when applied in the manner of the present invention.

Figure 3:
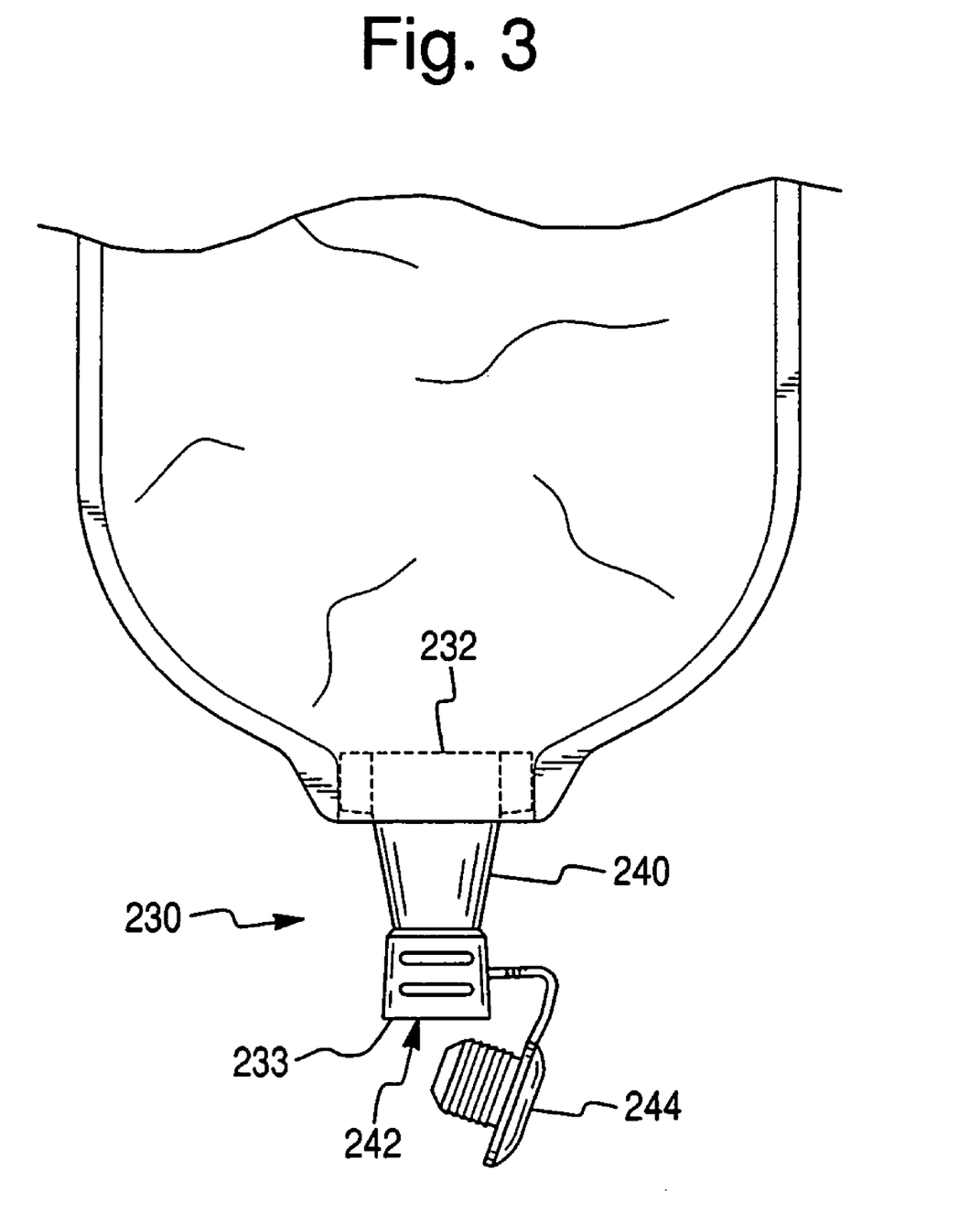
FIG. 3 is a detail view of a portion of the collection reservoir of the urine collection chamber of FIG. 1 and an exit conduit of the urine collection chamber of FIG. 1.

As seen best in FIG. 3, the urine collection chamber 200 further includes an exit conduit 230 configured to enable intermittent drainage of urine out of the collection reservoir. The exit conduit 230 can be composed of tubing extruded from a material resin similar to that of the collection reservoir 220, for example, PVC. The area of the collection reservoir 220 leading to the exit conduit 230, and the exit conduit 230 itself, can have a tapered shape to enable complete drainage of the collection reservoir 220. This tapered shape also facilitates even distribution of urine within the collection reservoir 220 to reduce "bag bulge," facilitating a discrete profile when the collection reservoir is worn under clothing. The tapered shape eliminates corners in the bottom of the collection reservoir 220 so that pooling of urine, which can occur in the corners of conventional collection reservoirs, does not occur in the collection reservoir 220.

To facilitate drainage of the collection reservoir 220, the exit conduit 230 can comprise an outlet tap 240. The outlet tap 240 includes an inlet 232, an outlet 233, a passage 242 extending between the inlet and the outlet, and a plug or cap closure 244 that can be releasably coupled to the outlet 233. When the plug 244 is coupled to the outlet 233, the plug 244 seals shut the collection reservoir 220. When the plug 244 is released from the outlet 233, urine can be drained out of the collection reservoir 220.

The outlet tap 240 has a durometer, or hardness measurement, compatible with the ergonomic requirements for placement in the pre-pubic to perineal area, particularly during sitting, transfers and other changes in body position. More particularly, the outlet tap 240 has durometer measurements of less than or equal to approximately 60 Shore A durometer.

In addition, the exit conduit 230 and its outlet passage 242 are configured so that a urinary drainage tubing connector of an additional conventional urine collection chamber (not shown), such as a leg bag, can be attached to the urine collection assembly 10. For example, the outlet passage 242 may receive in a friction fit or in an interference sealing fit the urinary drainage tubing connector of the additional conventional urine collection chamber. The capability of the outlet passage 242 to reversibly seal to such a drainage tubing connector allows the collection of a larger volume of urine, providing for longer periods of urine collection.

The urine collection chamber 200 also includes an anti-reflux valve 260. The anti-reflux valve 260 provides a fully operational, flexible, anti-reflux function in close approximation to the urine collection device 100; that is, the valve 260 prevents urine from backing up out of the urine collection chamber 200 and into the urine collection device 100. More specifically, the anti-reflux valve 260 communicates with the entrance conduit 210 to receive urine from the entrance conduit 210 and to prevent reflux of urine from the collection reservoir 220 into the entrance conduit 210. As seen in FIG. 1, the anti-reflux valve 260 can be disposed within the collection reservoir 220 and can be coupled, either directly or indirectly, to the entrance conduit 210. For example, the anti-reflux valve 260 can be contiguous with the entrance conduit 210. The flexible anti-reflux valve 260 is configured to provide consistent anti-reflux capability during ergonomic conformation to the complex shape of the pre-pubic to perineal area when the urine collection chamber 200 is located in positions of intended use, i.e., is attached to a urine collection device 100 that is attached to a user. Further, the anti-reflux valve 260 provides anti-reflux functions throughout the anticipated range of body positions of the user.

The anti-reflux valve 260 can be a flutter valve, a ball valve, a flap valve, or any other suitable one direction flow valve. The anti-reflux valve 260 preferably is very flexible to be compatible with the remaining structures of the flexible collection chamber 200 and the chamber's ergonomic requirements. The valve 260 can be comprised of a highly flexible material, such as the PVC or PVDC film used to make the collection reservoir 220, providing for effective function even when the collection chamber conforms to the curves required by the body's contours, while held in close proximity to the body below the user's waist and above the user's knees, as the user moves to any body position.

As can be seen in FIGS. 1 and 2, the valve 260 comprises two layers or flaps of thin film welded along two lateral sides 262 with an open distal side 263 and a proximal side 264 sealed to the entrance conduit 210. When pressure is created within the collection reservoir 220, the flaps seal together at their distal side 263. The pressure of urine in the collection reservoir 220 keeps the anti-reflux valve flaps closed together. Because urine is directed immediately through the anti-reflux valve 260 without any significant length of descent through urinary drainage tubing (which would cause an accumulation of negative pressure within the lumen of collection device 100), the anti-reflux valve 260 eliminates the Siphon Effect by preventing negative pressure in the urine collection device 100. Moreover, the proximity of the anti-reflux valve 260 to the urine collection device 100 protects genito-urinary tissue from the effects of negative pressure. In an alternative embodiment, the anti-reflux valve 260 may be contiguous with urine collection device 100.

A vent may be located in the entrance conduit 210, as shown in FIG. 2 as item 214, or in collection chamber 220, as shown in FIG. 2 as item 218. Either vent 214 or 218 will allow the ingress of air into the inner lumen of the urine collection assembly 10 to further relieve any relative negative barometric pressure that may develop within the lumen of the urine collection assembly 10 as a result of the above-described barometric phenomenon. In addition, the vent 214 prevents the accumulation of relative negative barometric pressure within the lumen of the urine collection device 100, and the vent 218 prevents the accumulation of relative negative barometric pressure within the lumen of the collection reservoir 220. Vents 214 and 218 are configured so as to prevent the ingress of foreign material, including microbes, into the lumen of the urine collection assembly 10. Vents 214 and 218 can function without allowing leakage of urine from the lumen of the urine collection assembly 10.

The urine collection chamber 200 may be manufactured as a single unit. The individual parts of the urine collection chamber 200, such as the collection reservoir 220, the entrance conduit 210, and the exit conduit 230, may be manufactured separately and then sealably bonded as one unit. For example, the components of the urine collection chamber 200 may be sealably assembled together by radio frequency welding, impulse welding or heat sealing processes.

The urine collection assembly 10 recognizes several advantages over known urine collection assemblies. For example, the urine collection chamber 200 is configured to accommodate individuals with delicate and/or neuropathic (decreased sensation) skin. The pre-pubic to perineal area is characterized by delicate skin. Items worn in this area may be forced to bear the weight of the torso of a sitting individual. For the individual with delicate skin, items of high durometer with acutely angled or "sharp" edges may cause discomfort and tissue injury. For the individual with neuropathic, or otherwise reduced skin sensation, an item with a high durometer and sharp edges may cause serious skin injury due to the inability to feel pain. In this regard, the urine collection chamber 200, including the collection reservoir 220, is smoothly contoured. Smoothly contoured is defined as having no sharp edges.

In addition, due to the close proximity of the urine collection device 100 and the urine collection chamber 200, the negative pressure/suction phenomenon caused by the vertical descent of urine from a urine collection device through 18 to 24 inches of urinary drainage tubing to a conventional urine collection chamber are avoided. Thus, the urine collection assembly 10 reduces or eliminates the negative pressure/suction phenomenon (the Siphon Effect) that can occur within the lumen of the urinary drainage tubing of conventional urine collection assemblies.

Since the urine collection chamber 200 contains an anti-reflux valve 260 that is positioned immediately proximate to the urine collection device 100, the urine collection assembly 10 also reduces urine reflux. Close proximity of the anti-reflux valve 260 to the urine collection device 100 prevents relative negative barometric forces from impinging on urinary tract or external genitourinary tissue. Thus, the urine collection assembly 10 avoids the resulting internal or external irritations associated with the use of urine collection bags distant from a urine collection device. Therefore, the urine collection chamber 200 can function effectively and not generate urine collection device torque or hasten detachment.

Further, since the urine collection chamber 200 can be worn close to, and can conform to, the user's body, the user's urine is contained in a discreet fashion. For example, the urine collection chamber 200 of the urine collection assembly 10 can be worn unobtrusively in the pre-pubic to perineal area. Moreover, the urine collection chamber 200 of the assembly 10 has a capacity sufficient for the needs of those with significant incontinence and mild to moderate stress incontinence (for example, a urine capacity of 1000 cc).

The urine collection chamber 200 can be used in conjunction with additional conventional urine collection chambers, such as standard leg bags, thigh bags and bedside bags. These additional urine collection chambers are attached via a standard urinary drainage connector or stepped adaptor that is attached to urinary drainage tubing. The lumen of the urinary drainage tubing is contiguous with the lumen of the additional collection chamber. The urinary drainage connector of the urinary drainage tubing of the additional urine collection chamber can be inserted into the outlet passage 242 of the outlet tap 240 after removal of the plug 244 from the outlet passage 242 (as shown in FIG. 3). The outlet passage 242 has the appropriate internal diameter so as to make a leak-proof seal when a urinary drainage connector for an additional collection chamber is inserted into the passage 242.

The urine collection chamber 200 can employ a variety of adaptors 212 that are capable of making a sealed connection to internal (intra-urethral and suprapubic) incontinence catheter devices and to external incontinence devices, including condom catheters. Some adaptors may be suitable for use with both internal and external devices, and some adaptors may be more suited for employment with one or the other of these two types of devices. Moreover, the entrance conduit 210 and the contiguous neck portion 225 of the collection reservoir 220 have a narrow profile, minimal cross-sectional area, and an absence of sharp edges or welds so as to be compatible with the requirements for allowing the collection chamber to travel up a user's retraction channel (i.e., the potential space within the skin folds of the panniculus adiposis or scrotum of a male with retracted anatomy) without causing skin injury or drag forces against the sides of the retraction channel. In one embodiment, the entrance conduit 210 and the contiguous neck portion 225 have a minimal cross-sectional area such that any point within three inches of the attachment site 150 of the urine collection device 100 to the penis 50 has no cross-sectional dimension exceeding two inches, and the entrance conduit 210 has no cross-sectional dimension exceeding three inches, and more preferably no cross-sectional dimension exceeding ¾ inch. By avoiding these drag forces, premature dislodgement of external incontinence devices and/or condom catheters can be avoided. Thus, the urine collection assembly 10 is compatible with male retracted anatomy.

Further, because the urine collection chamber 200 has a short, soft and flexible entrance conduit 210 and exit conduit 230, the urine collection assembly 10 significantly reduces skin injury and external urine collection device dislodgement risks in those users who lack skin sensation and those who have skin sensation but lack an ability to communicate discomfort and/or move. In one embodiment, the exit conduit 230, including the plug 244, does not exceed 1⅜ inches in total length, and all components of the exit conduit 230 have a durometer of less than or equal to 60 Shore A. Also, in one embodiment, the entire length of the entrance conduit 210, including the adaptor 212, does not exceed 1¾ inches and has a durometer of less than or equal to 60 Shore A, and the adaptor 212 does not exceed 1⅛ inches in length.

In an embodiment of the subject invention, the collection chamber can be employed for the collection of bodily fluids other than urine in conjunction with fluid collection devices including, but not limited to, pleurocentesis catheters, biliary tree drainage stents, wound drains and stents.

A urine or fluid collection chamber connected to a urine or fluid collection device will gradually increase in weight when the urine or fluid collection chamber fills with urine or fluid expelled from the user. A support device in accordance with the invention can be employed to prevent dislodgement of external urine or fluid collection devices and to prevent undesired traction on indwelling urine or fluid collection devices.

A urine or fluid collection chamber in close approximation to the skin of a user may represent a source of potential irritation or injury to the user. In order to prevent injury or irritation to the skin of the user due to the collection of perspiration moisture between the user's skin and the film surface of the fluid collection chamber, the support device comprises a support mechanism, such as a sleeve, composed of soft materials that envelops the urine or fluid collection chamber and reduces contact between the urine or fluid collection chamber and the skin. The support device also comprises a suspension mechanism, such as a belt, worn on the user's body to suspend the sleeve and bear the weight of the urine or fluid collection chamber.

The weight of urine or fluid collected by the collection chamber may cause premature dislodgement of an external urine or fluid collection device, or trauma at the insertion point of an indwelling urine or fluid collection device. The support device of the preferred embodiment provides support of the collected urine or fluid so that the weight of the collected material is not transmitted to the body attachment point of an external urine collection device or to an internal urine collection device. Thus, dislodgement of external or internal urine or fluid collection devices is averted. Risk of injury to external collection device attachment sites is avoided, and injury to internal structures contacting the indwelling urine or fluid collection devices is also avoided.

The distance between the urinary opening and the waist of a user of the urine collection chamber 200, referred to herein as the rise, differs from user to user. In order to effectively support the weight of excreted urine for all users of the urine collection chamber 200, the support device must be fully adjustable to accommodate for the difference in rise for each user of the urine collection chamber 200.

FIGS. 7-10 illustrate a support device having a suspension mechanism, such as belt 300, and a support mechanism, such as support sleeve 400. The support mechanism supports the urine or fluid collection chamber relative to the suspension mechanism and transmits the weight load of the collection chamber and any collected urine or fluid to the suspension mechanism.

Figure 7:
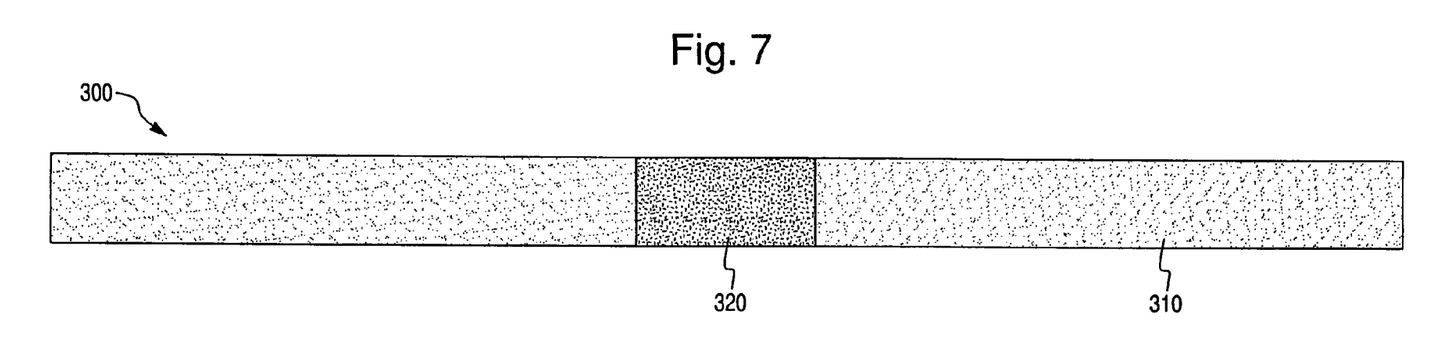
FIG. 7 is an elevation view of the outer side of a suspension belt of a support device for the urine collection chamber.
Figure 8:
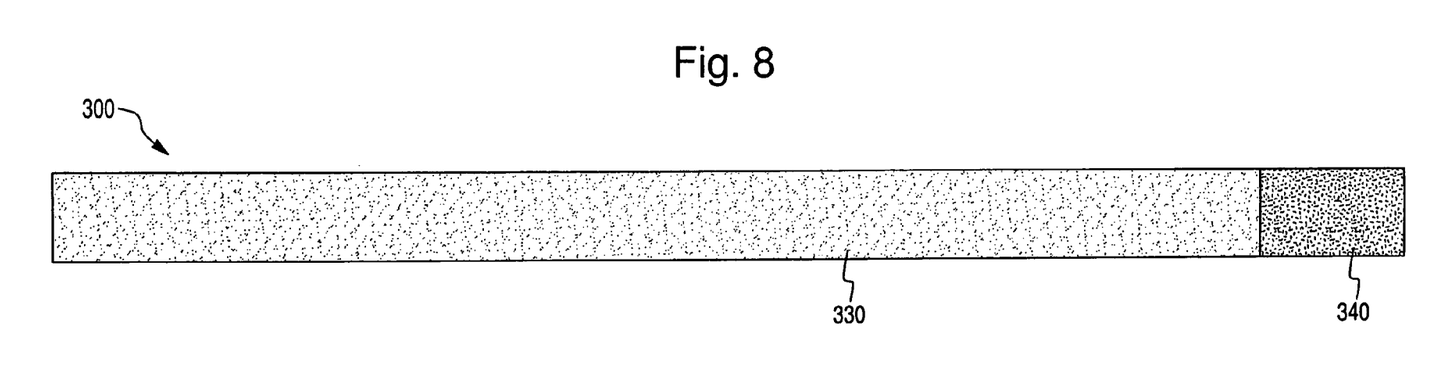
FIG. 8 is an elevation view of the inner side of the suspension belt of FIG. 7.

FIGS. 7 and 8 illustrate a preferred embodiment of a suspension mechanism in the form of a belt 300. The belt 300 can be worn circumferentially on the waist of a user, is constructed of a soft material having a sufficient width, thickness, weave, elasticity and softness that will not cut or irritate the user's skin, and has a flexural modulus and tensile strength sufficient to support a urine or fluid collection chamber in a fixed position when the chamber is filled to any portion of the chamber's capacity ranging from empty to completely full. The material of the belt 300 also has moderate elasticity to enable the user to comfortably cinch the belt 300 around the user's waist. One embodiment of the belt 300 comprises a two inch wide woven spandex-cotton blend elastic band with a loop surface 310.

Figure 9:
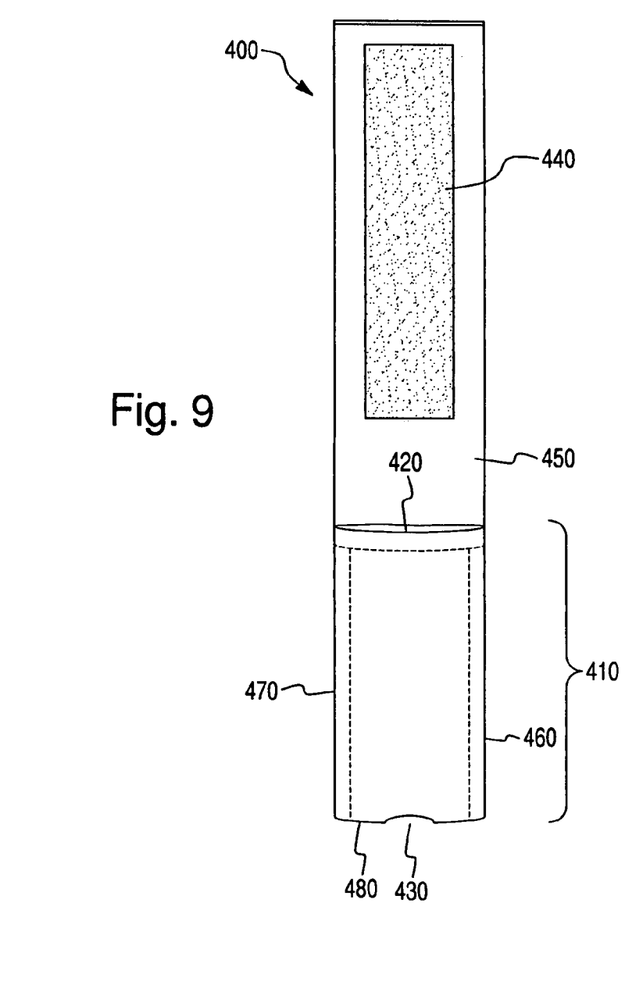
FIG. 9 is a front elevation view of the inner side of a support sleeve of a support device for the urine collection chamber.

FIG. 7 illustrates the outer side of suspension belt 300 worn away from the user's body, and FIG. 8 illustrates the inner side of the suspension belt facing the user's body. The belt 300 is shown lying flat in an open position. In the preferred embodiment, the belt 300 has a first strip 320 constructed of hook material capable of connection with a strip 440 of loop material on the support sleeve 400, as illustrated in FIG. 9. The outer side of the belt 300 has a loop surface 310 that is capable of adjustable connection with a second strip 340 of hook material on the inner side of the belt 300, as shown in FIG. 8. The second strip 340 can be adjustably connected to any portion of the loop surface 310 to provide a secure fit around the user's waist, for example, within a range of waist sizes from 26-56 inches.

FIG. 9 illustrates an embodiment of the support sleeve 400. The support sleeve 400 may be permanently affixed to the belt 300, or, as shown in the illustrated embodiment, the support sleeve 400 may be adjustably connected to the belt 300. Also, as mentioned above, the support sleeve 400 includes a strip 440 of loop material for connection to strip 320 of the belt 300. The support sleeve 400 generally comprises an elongated panel 450 folded over at one end to form a pocket 410 to receive a urine or fluid collection chamber. In an alternative embodiment, the pocket 410 could be formed by a small panel sewn on three sides to the elongated panel 450.

The woven construction of the support sleeve 400 and its pocket 410 does not stretch or yield when bearing weight and maintains an even distribution of fluid excreted in the urine or fluid collection chamber, as well as provides suspension in a fixed location, transferring the burden of bearing weight from the urine collection device to the support mechanism. In one embodiment, the support sleeve 400 is constructed of a lightweight woven cloth, such as cotton, that provides comfort and protection from moisture that may accumulate between the skin and the plastic or film construction of the urine or fluid collection chamber. That is, the support sleeve 400 can be comprised of a material such as cotton that provides a wicking effect to keep perspiration from collecting between the urine or fluid collection chamber and the user's skin. The support sleeve 400 also can be comprised of a material that enables absorption of fluid.

The support pocket 410 can be formed by folding over an end of the panel 450 and permanently fastening the folded over end to both edge 460 and 470 of the panel 450. The support pocket 410 includes an access opening 420 to receive the fluid or urine collection chamber. The support sleeve 400 also can have an opening 430, such as a buttonhole opening, that extends through the pocket 410, for example, at edge 480. When the urine collection chamber 200 is inserted into the pocket 410 via access opening 420, the outlet conduit 230 can extend through the opening 430.

Figure 10:
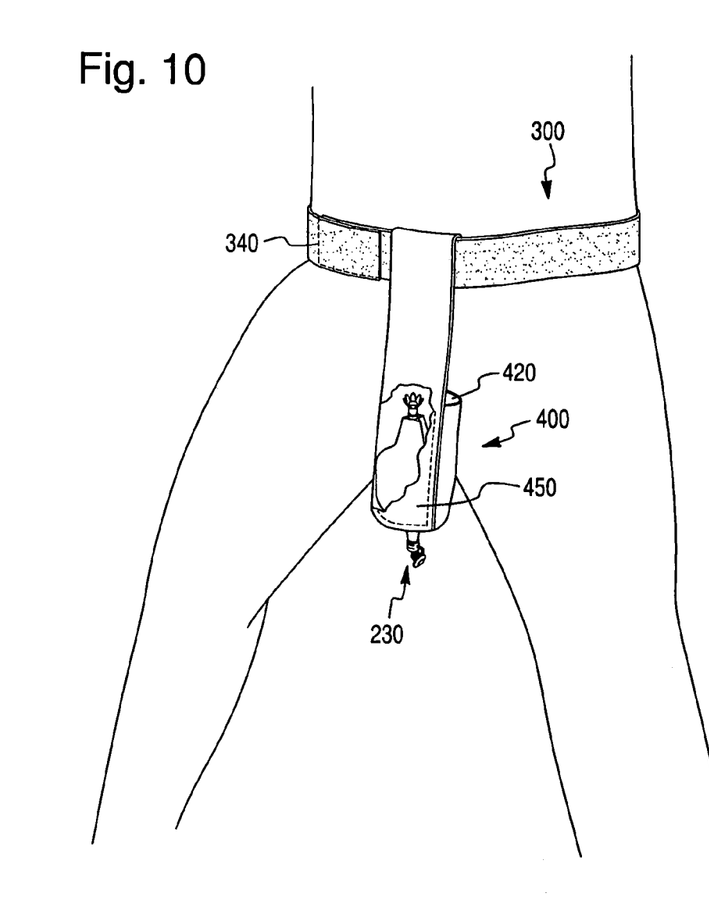
FIG. 10 is a perspective view of the urine collection chamber supported on a user's body by a support device according to an embodiment of the invention, in which the support sleeve connects to the suspension belt and contains the urine collection chamber.

FIG. 10 illustrates the cooperation between suspension belt 300 and support sleeve 400. The suspension belt 300 is secured to the user's body via attachment of second strip 340 to loop surface 310. The strip 440 of the support sleeve 400 connects to first strip 320 at a position chosen by the user based on the user's height and the distance between the waist and the urine collection chamber 200. In this manner, the weight of the urine collection chamber 200 is fully supported by belt 300 and sleeve 400, and the urine collection chamber 200 is maintained and supported in close approximation to the urine collection device and its attachment site (i.e., its attachment/insertion point) to the user's body. Any portion of support sleeve 400 that extends above suspension belt 300 upon connection of the first strip 320 and the support sleeve strip 440 can be folded over the belt 300 and worn between the belt 300 and the user's waist.

As an alternative to the embodiment illustrated in FIGS. 7-10, the suspension mechanism can comprise belt similar to belt 300, and the support mechanism can comprise strips of material that connect at one end to the belt and connect at the other end to the urine collection chamber 200. For example, the strips of material can include one or more buttonholes, and the urine collection reservoir 220 can include buttons on its exterior surface for engagement in the buttonholes of the strips of material. As another alternative, the belt, the strips of material, and the urine collection chamber can be outfitted with snaps to facilitate securement of the strips of material to the belt and to the urine collection chamber. Other suitable fasteners are contemplated by this invention.

The embodiments described above have been set forth herein for the purpose of illustration. This description, however, should not be deemed to be a limitation on the scope of the invention. Various modifications, adaptations, and alternatives may occur to one skilled in the art without departing from the claimed inventive concepts. The scope and spirit of the invention are indicated by the following claims.

What is claimed is:

1. A urine collection assembly, comprising:
an external urine collection device for external attachment to a user's body to collect urine at the site where urine is released external to the user's body, said external urine collection device including a plurality of leaves for external attachment to the parameatal surface of a user's body and an outlet for urine drainage, said external urine collection device creating a parameatal seal with the user's body; and
a urine collection chamber that communicates with said external urine collection device, said urine collection chamber comprising:
a collection reservoir configured to be wearable in close proximity to the user's body below the waist and above the knees of the user and to hold urine excreted from a user and that drains through said outlet of said external urine collection device,
an entrance conduit having an inlet external to said collection reservoir to receive urine from said external urine collection device and having an outlet terminating in said collection reservoir, said inlet of said entrance conduit being removably connected directly to said outlet of said external urine collection device without any intermediary drainage tubing between said inlet of said entrance conduit and said outlet of said external urine collection device, an anti-reflux valve within said collection reservoir in communication with said entrance conduit to receive urine from said entrance conduit, and an exit conduit on said collection reservoir configured to enable drainage of said collection reservoir and attachment of said collection reservoir to an additional urine collection chamber, wherein said exit conduit is connectible in sealing relation to a connector of drainage tubing of said additional urine collection chamber;

wherein said collection reservoir is configured to fit entirely in the pre-pubic to perineal area of the user bordered by the most superior aspect of the symphosis pubis, the distal aspect of the coccyx, and the proximal medial thighs of the user, and said collection reservoir is of a composition to conform to ergonomic requirements for being worn in the pre-pubic to perineal area of the user;

wherein said entrance conduit and said exit conduit are comprised of a material with a durometer of less than or equal to 60 Shore A durometer, and wherein said urine collection chamber has a minimal cross-sectional area such that any point within three inches of the site where said external urine collection device is attached to the user's body has no cross-sectional dimension exceeding two inches, and said entrance conduit has no cross-sectional dimension exceeding three inches.

2. The urine collection assembly according to claim 1, wherein said collection reservoir is generally elliptical in shape.

3. The urine collection assembly according to claim 1, wherein said entrance conduit is sealed to said anti-reflux valve in contiguous relation.

4. The urine collection assembly according to claim 1, wherein said collection reservoir includes a neck portion coupled to said entrance conduit, said entrance conduit and said neck portion comprise radiused welds, and said entrance conduit and said neck portion are flexible and are configured to ergonomically conform to the retraction channel formed by the tract of skin or space formed around the penis by the panniculus or scrotum as the penis retracts.

5. The urine collection assembly according to claim 1, wherein said entrance conduit includes an adaptor defining said inlet of said entrance conduit.

6. The urine collection assembly according to claim 1, wherein said collection reservoir is comprised of a polyvinyl chloride film.

7. The urine collection assembly according to claim 1, wherein said collection reservoir is comprised of an ethylene vinyl acetate multi-laminate film.

8. The urine collection assembly of claim 1, wherein said entrance conduit includes a vent external to said collection reservoir to provide relief of relative negative barometric pressure within said external wine collection device, without allowing leakage of urine out of said urine collection assembly.

9. The urine collection assembly of claim 1, wherein said collection reservoir includes a vent to prevent accumulation of relative negative barometric pressure within said collection reservoir, without allowing leakage of urine out of said urine collection assembly.

* * * * *